United States Patent
Risman et al.

(10) Patent No.: US 10,347,010 B2
(45) Date of Patent: Jul. 9, 2019

(54) ANOMALY DETECTION IN VOLUMETRIC IMAGES USING SEQUENTIAL CONVOLUTIONAL AND RECURRENT NEURAL NETWORKS

(71) Applicant: Realize, Inc., Chicago, IL (US)

(72) Inventors: Alexander Risman, Chicago, IL (US); Sea Chen, Chicago, IL (US)

(*) Notice: Subject to any disclaimer, the term of this patent is extended or adjusted under 35 U.S.C. 154(b) by 0 days.

(21) Appl. No.: 15/715,400

(22) Filed: Sep. 26, 2017

(65) Prior Publication Data
US 2018/0033144 A1 Feb. 1, 2018

Related U.S. Application Data

(63) Continuation of application No. 15/710,821, filed on Sep. 20, 2017.
(Continued)

(51) Int. Cl.
*G06K 9/62* (2006.01)
*G06T 7/00* (2017.01)
(Continued)

(52) U.S. Cl.
CPC ............ *G06T 9/002* (2013.01); *G06K 9/6256* (2013.01); *G06N 3/0445* (2013.01); *G06N 3/0454* (2013.01); *G06N 3/08* (2013.01); *G06T 7/0012* (2013.01); *G06T 7/0014* (2013.01); *G06T 7/521* (2017.01); *G06T 11/003* (2013.01); *G06T 11/008* (2013.01); *G06T 15/08* (2013.01); *G16H 30/20* (2018.01); *G16H 50/20* (2018.01); *G06T 2207/10081* (2013.01); *G06T 2207/10088* (2013.01); *G06T 2207/10116* (2013.01); *G06T 2207/20081* (2013.01); *G06T 2207/20084* (2013.01); *G06T 2207/30016* (2013.01);
(Continued)

(58) Field of Classification Search
None
See application file for complete search history.

(56) References Cited

U.S. PATENT DOCUMENTS 9,336,482 B1 * 5/2016 Corrado .............. G06N 3/0445
2011/0257522 A1 * 10/2011 Berard-Andersen ........................ A61M 5/16859
600/438
(Continued)

FOREIGN PATENT DOCUMENTS

WO  WO-2015109254 A2 * 7/2015 ........ G01R 33/56308

OTHER PUBLICATIONS

Guler et al., "A recurrent neural network classifier for Doppler ultrasound blood flow signals", Pattern Recognition Letters 27 (2006) 1560-1571.

*Primary Examiner* — Tahmina N Ansari
(74) *Attorney, Agent, or Firm* — Brad Bertoglio

(57) ABSTRACT

Computer-implemented methods and apparatuses for anomaly detection in volumetric images are provided. A two-dimensional convolutional neural network (CNN) is used to encode slices within a volumetric image, such as a CT scan. The CNN may be trained using an output layer that is subsequently omitted during use of the CNN as an encoder. The CNN encoder output is applied to a recurrent neural network (RNN), such as a long short-term memory network. The RNN may output various indications of the presence, probability and/or location of anomalies within the volumetric image.

18 Claims, 9 Drawing Sheets

Related U.S. Application Data

(60) Provisional application No. 62/397,347, filed on Sep. 21, 2016.

(51) Int. Cl.
| | |
|---|---|
| *G06T 9/00* | (2006.01) |
| *G06N 3/04* | (2006.01) |
| *G06T 7/521* | (2017.01) |
| *G06T 15/08* | (2011.01) |
| *G16H 50/20* | (2018.01) |
| *G06N 3/08* | (2006.01) |
| *G06T 11/00* | (2006.01) |
| *G16H 30/20* | (2018.01) |

(52) U.S. Cl.
CPC ............... *G06T 2207/30061* (2013.01); *G06T 2207/30064* (2013.01)

(56) References Cited

U.S. PATENT DOCUMENTS

| | | | | |
|---|---|---|---|---|
| 2016/0140425 | A1* | 5/2016 | Kulkarni | G06K 9/4628 382/159 |
| 2017/0076043 | A1* | 3/2017 | Dormer | G06F 21/6254 |
| 2018/0033144 | A1* | 2/2018 | Risman | G06T 15/08 |
| 2018/0082443 | A1* | 3/2018 | Risman | G06T 15/08 |

\* cited by examiner

| Architecture | Input Size (ZxYxX) | Model Parameters | Number of Epochs | Training Time (per epoch) | Inference Time (for one example) | Cross-entropy Loss | ROC AUC | FROC |
|---|---|---|---|---|---|---|---|---|
| 3D CNN A | 6x20x20 | 4,255,044 | 12 | 2,709 | .00537 | .0262 | .964 | .623 |
| 3D CNN B | 10x30x30 | 5,100,144 | 12 | 4,338 | .00698 | .0167 | .975 | .707 |
| 3D CNN C | 26x40x40 | 23,660,144 | 12 | 15,363 | .0113 | .0114 | .982 | .748 |
| CNN-LSTM A | 22x32x32 | CNN: 980,386 LSTM: 3,412,994 | CNN: 15 LSTM: 20 | CNN: 765 LSTM: 2,061 | .0222 | .00832 | .980 | .677 |
| CNN-LSTM B | 32x48x48 | CNN: 1,579,906 LSTM: 3,740,674 | CNN: 15 LSTM: 20 | CNN: 1,080 LSTM: 2,862 | .0368 | .00758 | .978 | .721 |
| CNN-LSTM C | 42x64x64 | CNN: 3,193,378 LSTM: 4,199,426 | CNN: 15 LSTM: 20 | CNN: 1,476 LSTM: 3,717 | .0573 | .00737 | .974 | .719 |
| 3D CNN Ensemble | N/A | N/A | 12 | 22,410 | .0235 | .00832 | .981 | .794 |
| CNN-LSTM Ensemble | N/A | N/A | CNN: 15 LSTM: 20 | CNN: 3,321 LSTM: 8,640 | .116 | .00560 | .989 | .793 |
| Full Ensemble | N/A | N/A | N/A | N/A | .140 | .00549 | .992 | .852 |

FIG. 12

ANOMALY DETECTION IN VOLUMETRIC IMAGES USING SEQUENTIAL CONVOLUTIONAL AND RECURRENT NEURAL NETWORKS

TECHNICAL FIELD

The present disclosure relates in general to detection of anomalies in volumetric images, and in particular to methods and apparatuses for identifying anomalies such as medical conditions within medical volumetric images, such as CT and MRI scans.

BACKGROUND

Recent advances in imaging techniques have enabled more rapid and higher-resolution volumetric imaging in a variety of applications, such as medical imaging. Image data may be processed electronically to facilitate various visualizations. One such task is segmentation, in which areas of an image are classified as being a member of a given class or not. For example, each brain MRI includes a hippocampus, and a segmentation task may identify the portion of the MRI corresponding to the hippocampus.

Another type of task that may be applied to volumetric imaging is anomaly detection. Anomaly detection tasks typically seek to determine a probability that a given 3D image belongs to a class, such as presence of a disease, anomaly or other condition of interest, where only some volumetric images are expected to exhibit the condition. However, to date, analysis of such images to identify anomalous conditions has largely relied on human analysis and expertise.

Moreover, individuals trained to review medical images, such as radiologists, tend to be highly skilled and highly paid. Using current approaches, their work may involve exhaustive manual review of potentially hundreds of image slices. As imaging systems are used with increased frequency, to generate increasing volumes of image data, the cost of traditional radiologist review may be burdensome. A limited supply of qualified radiologists analyzing an increasing volume of medical image data may lead to critical delays in analysis results, and possible negative impacts on the precision and recall of analysis results.

Computer aided detection and diagnosis (CAD) technologies have been used to facilitate diagnostic use of medical imaging data. Such technologies often rely on traditional image processing approaches, and are typically based on handcrafted, problem-specific heuristics and features. The use of these approaches has been hampered by high processing times, inaccuracy and non-generalizability. These issues may be exacerbated by rapidly rising data volumes generated by current high-resolution volumetric imaging devices. As a result, CAD technologies have become common for use only in a few specific applications, such as mammography.

SUMMARY

The present disclosure describes, inter alia, systems and methods for analysis of volumetric images, such as detection of an anomaly in a volumetric medical image. Various embodiments utilize neural network architectures that may include a model sequencing a convolutional neural network (CNN) with a recurrent neural network (RNN).

In accordance with one aspect of the disclosure, a computer-implemented method is provided for detection of an anomaly in a volumetric medical image. The volumetric image includes a spaced sequence of two-dimensional slice images. Each slice image is encoded using a two-dimensional regular CNN, to generate a sequence of encoded slices. The sequence of encoded slices is applied to a RNN, such as a long short-term memory (LSTM) network. The RNN output may be indicative of the presence or absence of the anomaly, such as a probability that the anomaly is present within the volumetric image, and/or a probability map indicative of the likelihood that various locations within the volumetric image correspond to the anomaly. The CNN may be trained using an output layer, which output layer may be subsequently omitted during use of the CNN as an encoder; thus, the CNN encoder's output may be taken from, e.g., the output of a final dense layer. The method may be applied to, e.g., head CT images to detect intracranial hemorrhage; or chest CT images to detect the presence of a lung nodule. The method may also be applied, alone or in an ensemble with other models, to reduce false positives in an anomaly detection application.

Another aspect of the disclosure addresses a computing device for anomaly detection in a volumetric image. The computing device includes a digital memory, and at least one processor coupled to the digital memory. The at least one processor is configured to execute instructions stored in the memory to perform steps such as those described in the above method.

Another aspect of the disclosure addresses training of a computer-implemented mechanism for detecting anomalies in a volumetric image, such as a medical image. First, an initial two-dimensional regular CNN is trained using a training set of slice images with a first set of slice-level labels. The first set of slice-level labels may include, e.g., a binary indicator of whether a slice contains evidence of a disease, or a segmentation mask designating portions of a slice containing evidence of a disease. The trained CNN is then used to encode slice images in a training set of volumetric images, which may be applied to an RNN, such as a LSTM. The CNN may be modified for use as an encoder by removing an output layer that had been used to train the CNN, leaving a last dense layer from which the RNN input is derived. The second set of RNN training labels may include, e.g., a single series-level indication of whether a volumetric image contains a given disease or a probably that such a disease is contained. The RNN output may include, e.g., slice-by-slice probabilities of the presence of a particular disease, anomaly or condition, and/or a segmentation map indicative of disease location within the volumetric image.

Another aspect of the disclosure involves training a neural network sequence that includes a CNN having a final dense layer, connected to a RNN input layer. Initial coefficients may be loaded into the CNN, and then the neural network sequence may be trained as a whole.

Various other objects, features, aspects, uses and advantages of the present invention and embodiments will become more apparent from the following descriptions of preferred embodiments, along with the accompanying drawings.

BRIEF DESCRIPTION OF THE DRAWINGS

FIG. 12 is a table of model and ensemble performance in a trial of false positive reduction for lung node detection on chest CTs.

DETAILED DESCRIPTION

Figure 1:
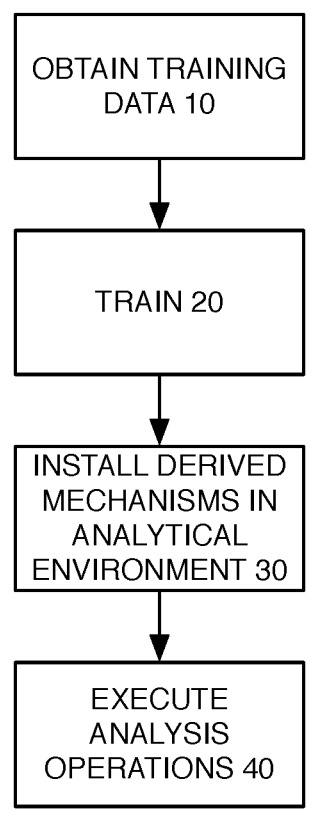
FIG. 1 is a process for implementing a machine-learning based system for analyzing volumetric image data.

While this invention is susceptible to embodiment in many different forms, there are shown in the drawings and will be described in detail herein several specific embodiments, with the understanding that the present disclosure is to be considered as an exemplification of the principles of the invention to enable any person skilled in the art to make and use the invention, and is not intended to limit the invention to the embodiments illustrated.

In accordance with some embodiments, a novel combination of deep learning techniques can be effectively used to detect anomalies in volumetric images, such as medical CT and MRI scans. Data sets in such medical studies may include 3-dimensional ("3D") volume objects represented by a series of two-dimensional ("2D") images (sometimes referred to as "slices") taken along some defined axis. Models may be produced given appropriate training data and labels, to identify, and optionally locate, anomalies within such data sets.

In particular, techniques have been identified to apply features extracted by convolutional neural networks, to recurrent neural networks, to provide high levels of classification performance, particularly when utilized in connection with certain pre-training processes. Such implementations may be highly effective on a variety of 3D image classification tasks, with little or no requirement for hand-crafted task-specific features.

Volumetric image analysis results obtained from the systems described herein may be useful in a variety of ways. For example, in the context of medical imaging analysis with a constrained supply of radiologists, system results may be utilized to prioritize scans with a high probability of important pathology, thereby reducing wait times for radiologist review of critical results. System results may also be utilized to increase the confidence of physicians who are not trained radiologists in interpreting CT or MRI results, so they can more rapidly enact medical intervention. System results may also be used to highlight areas within a volume having the highest likelihood of a pathology finding, potentially reducing the amount of time required by a radiologist to interpret the imaging data, while reducing opportunities for a trained radiologist or other medical professional to inadvertently miss a potential pathologic finding. Embodiments may be utilized for these and other purposes.

Clinical applications for which embodiments may be effective include detection of intracranial hemorrhage (ICH). Expeditious interpretation of head CT images may facilitate rapid initiation of treatment for ICH, which is often critical to patient outcome. Lung cancer screening with low dose chest CT is another clinical application for which embodiments may be effectively employed. The National Lung Screening Trial (NLST) has found a 20% reduction in deaths from lung cancer in the high risk smoking population when using low dose CT as compared to chest X-ray for screening. Because of this data, Medicare has approved reimbursements for CT screenings of these high-risk individuals. This population represents an estimated 7-10 million individuals, which may be obtaining yearly screening CT scans. Pulmonary embolism (PE) is another acute and potentially life-threatening disease process which requires rapid intervention with anticoagulation therapy. PE is also relatively common, and may be found on 10-20% of CT pulmonary angiography performed when PE is suspected. Difficulties in interpretation, including artifacts, can lead to false positives and overdiagnosis, which in turn may increase complications from anticoagulation. In each of these applications, and others, accurate and timely assessment of patient condition may be critical to optimal patient outcomes.

FIG. 1 illustrates, at a high level, a process that can be utilized in connection with embodiments described herein in order to implement an automated volumetric image analysis mechanism in a clinical environment. In step 10, a set of training data is obtained. In some embodiments, training data may be obtained as data sets published in connection with research. In some embodiments, training data may be obtained by clinical service providers in monitoring actual patients. One or more of these, or other mechanisms, may be utilized in step 10 to assemble a set of data that can be used for training. In each case, preferably the training data provides medical imaging scans, such as CT scans, and evaluated outcomes as determined by, e.g., expert radiologist review and/or subsequent patient monitoring and diagnosis.

In step 20, machine learning techniques are applied to the training data, as described further hereinbelow, in order to derive analysis mechanism coefficients that are predictive of patient pathology, as described further below. In step 30, the analytical mechanisms derived in step 20 are installed with an automated analytical environment. In step 40, automated analysis operations are executed.

Exemplary Computing Environment

Figure 2:
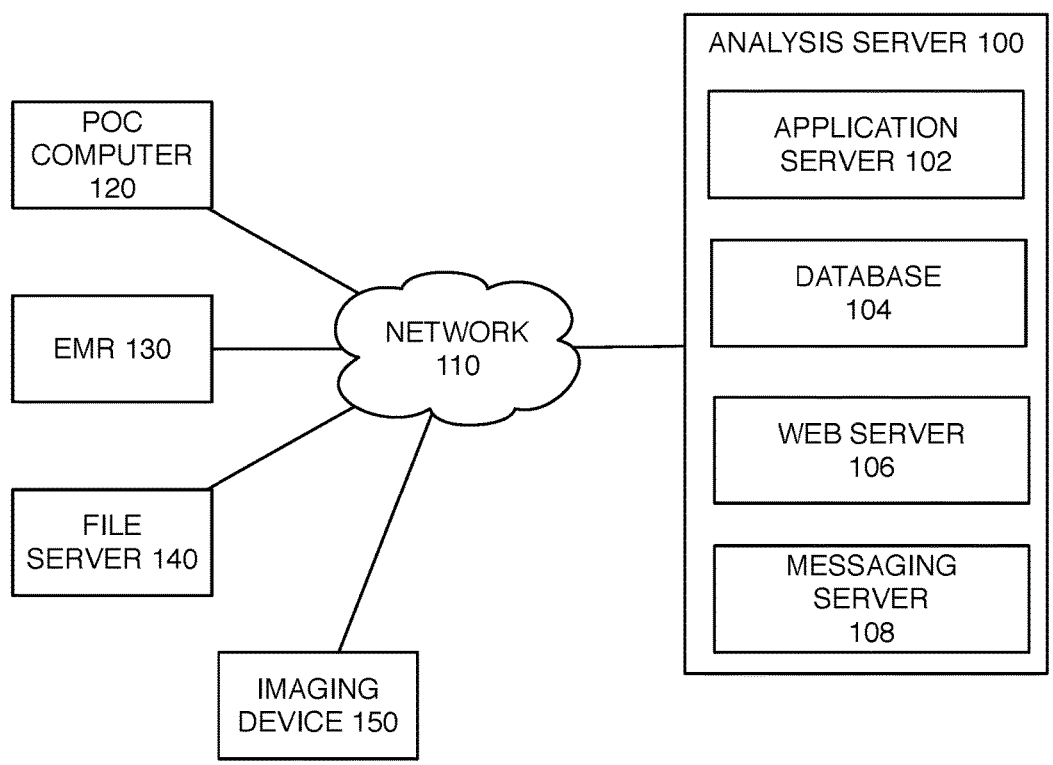
FIG. 2 is a schematic block diagram of a computing environment.

FIG. 2 illustrates an exemplary computing environment in which certain embodiments described herein may be implemented. Analysis server 100 is a computing server adapted for communication via network 110. Analysis server 100 may be located on a local network within a target user's premises (e.g. within a hospital, on a hospital intranet), or remotely (e.g. a cloud-connected service accessible via the Internet or other wide-area network).

Server 100 communicates with one or more other computing systems via network 110. A medical services environment may include one or more point of care (POC) computers 120. POC computers 120 may be installed at a particular patient's point of care (e.g., in patient rooms or within a bedside monitoring station). In some embodiments, POC computer 120 may be centrally located and utilized for multiple patients, such as a central ward monitoring computer installed for use with multiple patients in a particular hospital ward. In other embodiments, POC computer 120 will be a mobile device, such as a tablet computer utilized by health care service providers while moving within a facility. POC computer 120 could be installed within an ambulance, or in a triage facility for incoming ambulatory patients. In some embodiments, the computing environment may also include one or more of Electronic Medical Records (EMR) system 130 and/or file server 140. File server 140 may be, e.g., a Picture Archiving and Communication System ("PACS"), which is commonly used for storage and communication of medical images. The environment may also include one or more imaging devices 150, such as CT and MRI systems. One or more of POC computer 120, EMR 130, file server 140 and imaging devices 150 may be utilized as a source of data for analysis server 100, and/or as a destination for storing or otherwise conveying output results from analysis server 100.

Analysis server 100 may include application server 102, database 104, web server 106 and messaging server 108. Application server 102 implements functions and components described further hereinbelow. Database 104 provides a mechanism for local storage of data. Web server 106 may provide a web-based interface for interaction with analysis server 100 by, e.g., POC computer 120. Messaging server 108 may enable notifications to third party computing devices relating to system operation and/or image processing results. In some embodiments, messaging server 108 may be, or include, a PACS.

While depicted in the schematic block diagrams as a block element with specific sub-elements, as known in the art of modern web applications and network computing services, one of ordinary skill in the art could readily implement server 100 and other illustrated computing resources in a variety of ways in accordance with the present disclosure, including via distributed hardware and software resources and using any of multiple different software stacks. Server 100 and other computing resources may include a variety of physical, functional and/or logical components such as one or more each of web servers, application servers, database servers, email servers, storage servers, PACS, SMS or other instant messaging servers, and the like. That said, the implementation of server 100 and other computing resources will typically include at some level one or more physical servers or computers, having one or more microprocessors and digital memory for, inter alia, storing instructions which, when executed by the processor, cause the device to perform methods and operations described herein.

Analysis Mechanisms

Figure 3:
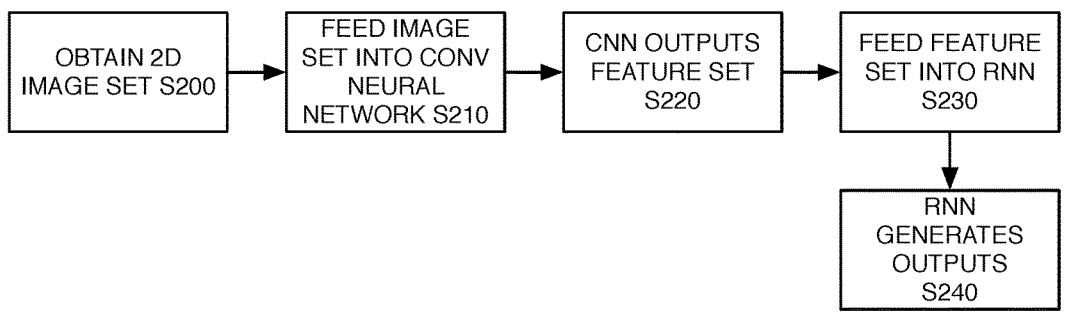
FIG. 3 is a process for analyzing volumetric image data.
Figure 4:
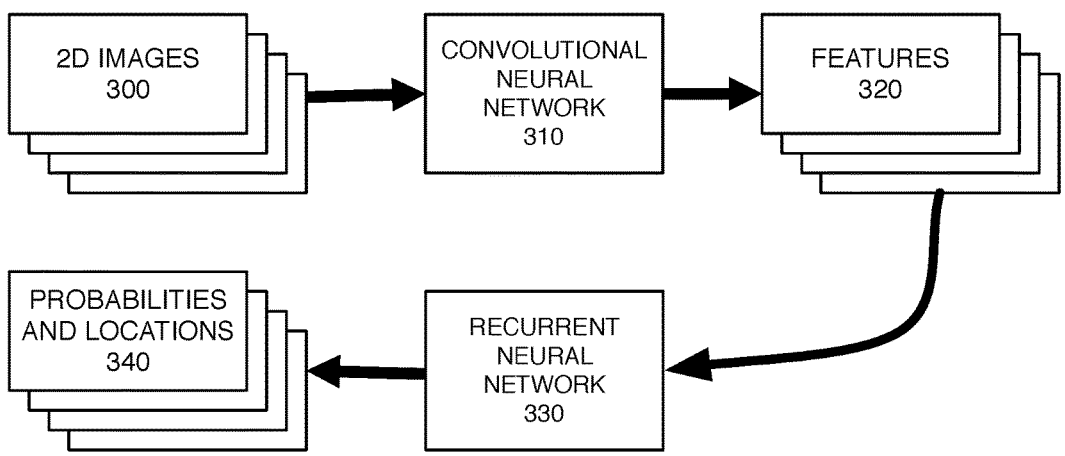
FIG. 4 is a schematic block diagram of a system for analyzing volumetric image data.

Analysis server 100 can implement models for analysis of volumetric data. Convolutional neural networks are a dominant paradigm in image analysis, and may be ideal for analyzing grid-like data. Recurrent neural networks are a dominant paradigm in text analysis, and may be ideal for analyzing sequential data. Models may combine these two deep learning architectures into a powerful tool for volumetric image analysis, such as detection of anomalies such as ICH, PE and lung nodules. Some embodiments may generally be described by the process of FIG. 3 and the schematic block diagram of FIG. 4.

In step S200, a set of 2D images 300 is obtained for analysis. Such images may be obtained by, for example, importing a set of CT or MRI images from electronic medical records system 130, file storage system 140, or medical imaging device 150.

In step S210, 2D images 300 are fed into convolutional neural network ("CNN") 310. CNN 310 is trained to extract a feature set from each image that is relevant to detection of particular anomalies. Exemplary training techniques, CNN configurations and parameters are described further below.

In step S220, CNN 310 generates output including feature set 320. Feature set 320 is an array including one or more features derived from each of 2D images 300.

In step S230, feature set 320 is fed through recurrent neural network ("RNN") 330. RNN 330 models dependencies across the entire sequence of 2D images 300. Exemplary training techniques, RNN configurations and parameters are described further below.

In step S240, RNN 330 generates an array of outputs 340. The nature of outputs 340 is dependent on the structure of the output layer of RNN 330. In some embodiments, outputs 340 may include the probability of a specified finding or anomaly existing within the entire image series 300. For example, in a medical imaging application, outputs 340 may include a probability of an intracranial hemorrhage being exhibited within image series 300. Outputs 340 may also include the probability of a specified finding (e.g. intracranial hemorrhage) within each 2D slice within image set 300. In some embodiments, outputs 340 may further include an estimated location of the finding within each slice, such as detecting the existence and estimated locations for each of one or more lung nodules in a thoracic CT scan.

Specific network architectures and methods of use are described in further detail hereinbelow.

System Training and Optimization

The overall process of FIG. 1 includes steps for obtaining training data (step 10) and training the automated analysis components described herein (step 20). A general training method, as well as specific optimizations and use cases, are described below.

Figure 5:
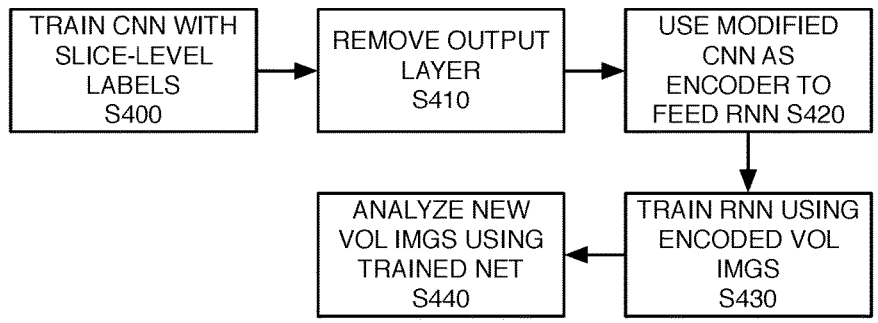
FIG. 5 is a process for training and utilizing a CNN-RNN model for analysis of volumetric images.
Figure 6:
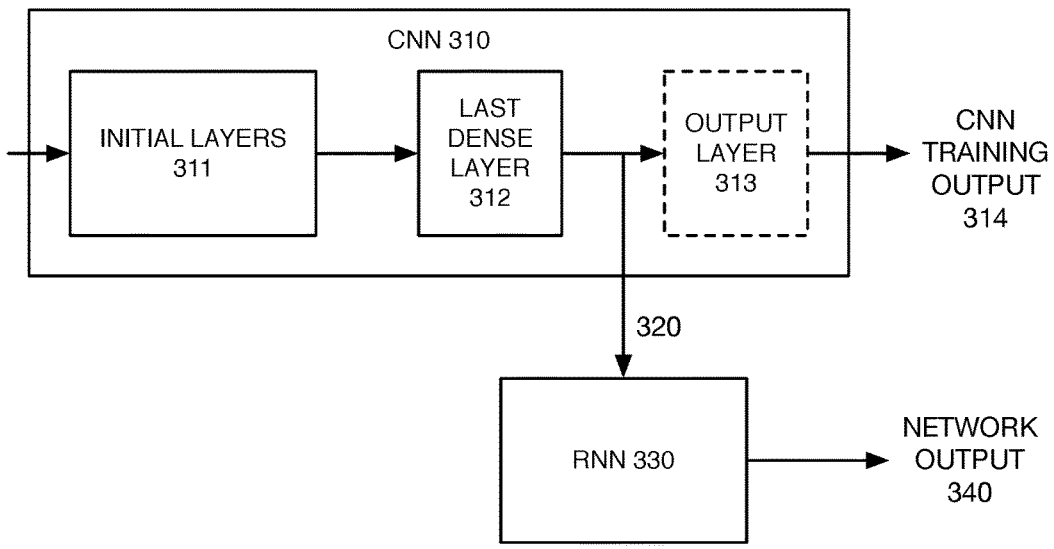
FIG. 6 is a schematic block diagram of a CNN-RNN model.

Generally, in some embodiments, training step 20 may include training of CNN 310, as well as training of RNN 330. One network architecture and training approach that may be particularly effective for anomaly detection in volumetric images is described generally in the process of FIG. 5. FIG. 6 is a schematic illustration of an exemplary configuration that may be applied to the network of FIG. 4, in which a modified CNN is used as an encoder for a subsequent RNN, such that it may be used to implement the process of FIG. 5. In particular, like the network configuration of FIG. 4, the network configuration of FIG. 6 uses a 2D CNN to feed a RNN; however, in the embodiment of FIG. 6, the RNN receives input from a portion of the CNN just before the output layer used for CNN training.

In step S400, 2D CNN 310 is trained on individual slices of a volumetric image, such as a CT scan, using slice-level labels. For example, in some embodiments, the slice-level labels may include a binary indicator of whether a particular slice contains evidence of a particular disease. In some embodiments, the slice-level labels may include segmentation masks marking the location in each slice containing indication of a disease. CNN 310 includes one or more initial layers 311, a last dense layer 312, and an output layer 313. CNN training output 314 is used as feedback in a supervised training process to optimize the performance of CNN 310.

Once CNN 310 is trained, it may be modified for use in training RNN 330 and/or in applying the trained network to new diagnostic data. In the embodiment of FIG. 5, in step S410, the output layer 313 of CNN 310 is removed to generate a modified CNN 310. For example, in embodiments for which slice-level labels include a binary indicator of disease present, the output layer 313 may be a single neuron representing the probability of an anomaly being present in the slice. In embodiments for which slice-level labels include segmentation masks, the output layer 313 may be a probability mask. After removing the output layer 313, the modified CNN's new output layer is the last dense layer 312 of CNN 310, which is situated immediately prior to the removed output layer. The output of last dense layer 312 may then be used as an output 320 of the modified CNN 310.

In step S420, the modified CNN 310 (and its output 320) is used as an encoder to feed RNN 330. Thus, modified CNN 310 may convert slice images fed into it into a representation having the dimension of the new output layer 312. For example, if the network was trained on 64×64 images and the last dense layer 312 before the original output layer 313 contained 512 hidden units, the encoder network in step S420 would represent 64×64 images as a 512 value vector, i.e. the encoding dimension of modified CNN output 320 is 512. The encoder is then used to encode each slice in each volumetric image fed to RNN 330. For example, if a given volumetric image initially consisted of 100 slices that were each 64×64 (i.e. an overall shape of 100×64×64) and the encoding dimension of modified CNN 310 is 512, the output 320 of modified CNN 310 would have a shape of 100×512. Thus, modified CNN 310 acts to (amongst other things) significantly reduce the data volume fed into RNN 330.

The encoded volumetric image may then be treated as a sequence of encoded slices, and a set of such encoded volumetric images can then be used to train a recurrent neural network 330, preferably a Long Short-Term Memory (LSTM) variety (step S430). This allows the overall network to incorporate 3D context in a way that cannot be accomplished with a 2D CNN. RNN 330 may then generate network output 340. Network output 340 may be used as feedback to train RNN 330, and/or for yielding diagnostic results of volumetric image analysis.

Various types of labels may be used in training such a network with this data. In the simplest case, a single, series-level label, such as whether or not a given volumetric image contains a given disease, will accompany each encoded series, and RNN 330 will then learn to predict the probability that a given volumetric image contains a disease. In some embodiments, labels may also take the form of a sequence of slice-level indicators of the presence of a disease, in which case RNN 330 will learn to predict slice-by-slice probabilities of the presence of a disease, incorporating the context of neighboring slices in these predictions, or even a segmentation map.

Architectures described herein using a neural network sequence comprised of a 2D CNN to feed a RNN may provide several favorable properties as compared to alternative approaches. In comparison to a 3D convolutional network, in practice, a 2DCNN-LSTM model has been found to achieve comparable classification performance in a lung nodule false positive reduction task, with an order of magnitude fewer parameters. (In some test cases, the 2DCNN-LSTM exhibited slightly better cross-entropy loss, equal ROC-AUC, and slightly worse FROC). But because the 2DCNN-LSTM model is so much smaller, larger patches around a nodule candidate can be analyzed with a given amount of computing resources, without running into memory issues. Such memory efficiency may provide an even greater advantage to the 2DCNN-LSTM architecture when applied towards segmentation tasks. In some use cases, predictions of a 2DCNN-LSTM model (as described herein) can be combined with 3DCNN predictions to achieve even better classification performance than either architecture on its own.

Some embodiments described above that use a regular convolutional front end may also provide benefits over a hybrid model having a fully-convolutional CNN portion. A fully convolutional network may take an image (i.e. a 2D matrix) as input and produce an image (i.e. another 2D matrix) as output, for the convolutional portion of the architecture (i.e. before the LSTM network). This requires that the subsequent LSTM use convolutional operators as well when analyzing each element of the input sequence. By contrast, regular convolution embodiments described herein take an image (i.e. a 2D matrix) as input and produce a 10 vector as output. This allows use of a standard LSTM with standard vector multiplication to analyze each element of the input sequence, dramatically reducing the memory consumption and computational power required to train the LSTM and use it for inference. This conservation of resources, particularly memory, can be extremely valuable when running models on large datasets of 3D images like CT scans.

Figures 7, 8:
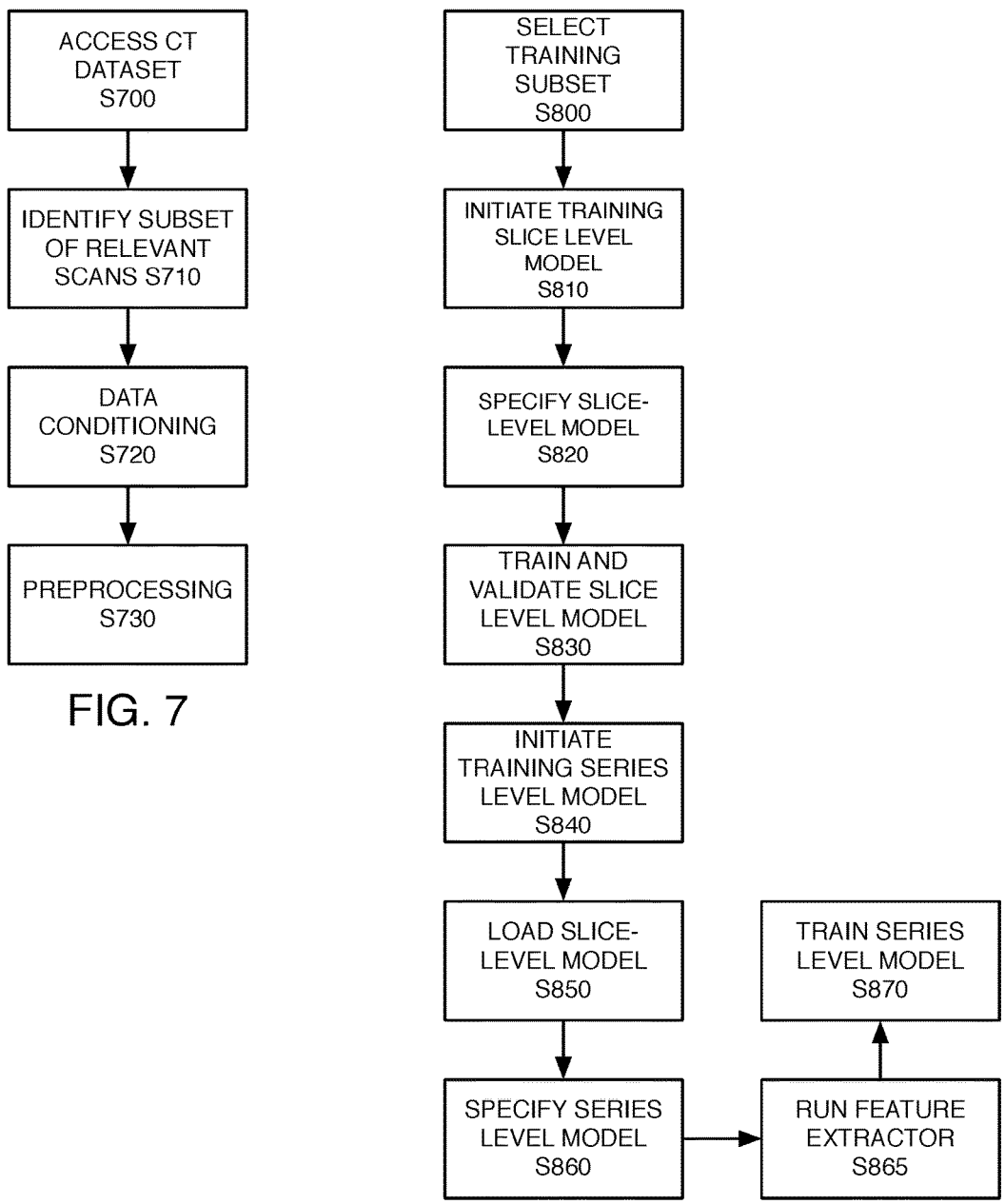
FIG. 7 is a process for selecting training data.
FIG. 8 is a process for training a system for analyzing volumetric image data.

As indicated above, the CNN and RNN models each require training prior to deployment for volumetric image analysis and classification. FIG. 7 illustrates further detail of an exemplary process for obtaining training data, in the context of detecting evidence of intracranial hemorrhage (ICH) from CT scan data. It is contemplated and understood that analogous processes and mechanisms can be readily utilized by persons of ordinary skill in the art, for detecting other conditions or anomalies from similar or different volumetric image data.

In step S700, a dataset of CT scans is accessed by server 100. Each CT scan may be composed of a series of 2D slices in the DICOM format (which stores the raw pixel data of a medical image as well as various metadata), and a set of labels produced by a radiologist for each scan. The labels may include optional slice-level annotations describing the location, within each slice, of evidence of an anomaly (if any), and a mandatory scan (i.e. series) level label classifying the scan as either not containing the anomaly or containing the anomaly and optionally what type of anomaly it is (if present). A detailed example implementation for each step will be provided in the context of an intracranial hemorrhage (ICH) detection application for CT head when appropriate.

In step S710, a subset of CT series is extracted for use in training on a given condition. Server 100 iterates over each series, checking selected metadata fields in the first DICOM file in the series to determine whether the series meets the criteria for inclusion in the training set. For ICH, this may be accomplished by, e.g., checking whether the ProtocolName and SeriesDescription fields contained certain strings like "head" or "brain" and did not contain certain strings like "chest" or "spine", as well as checking that the SliceThickness and SpacingBetweenSlices fields, representing the amount of tissue the slice represents, fell within an expected range of values. It may also be desirable to limit the dataset to series containing 154 or fewer slices.

If the series meets the specified inclusion criteria, the series image data is conditioned (step S720). For example, the raw image, represented as a 2D (height×width) array of pixels, may be extracted from each slice in the series. The image data may be up-or-downsampled to a common resolution, and then added to a 3D (number of images×height×width) array containing all images extracted thus far. To a separate 2D (number of images×number of metadata fields)

slice metadata array, metadata associated with each image may be added, including, but not limited to, the ID of the series and the index of the image in that series. To a third, series metadata array, the metadata associated with the series as a whole may be appended including, but not limited to, the ID of the series and whether or not it contains the anomaly in question.

In an exemplary embodiment of ICH detection, each slice can be downsampled to 64×64 pixels. For the series-level metadata, the series ID can be included, as well as whether or not the series contained evidence of ICH, and optionally a subtype of bleed. Analysis server 100 may iterate through the slice-level location annotations of the series for which they are provided and generate an array of metadata that includes series ID, slice index, whether or not the slice contained evidence of the anomaly, and, optionally, the coordinates of the anomaly within the slice.

In step S730, preprocessing operations are applied to the conditioned series image data. Exemplary preprocessing operations that may be desirable include denoising, segmentation, data normalization, and alignment.

Application of a denoising mechanism may be effective where, e.g., variation in pixel intensity due to electronic sensor noise decreases accuracy of the resulting model and/or degrades the ability of the training process to rapidly converge on an optimal model. Applications of various filters, as appropriate for the noise characteristics of the system, may enhance accuracy. The simplest of these filters, a low-pass filter to remove high-frequency components, can be applied to smooth the images prior to the neural network analysis.

In some embodiments, preprocessing may include a segmentation mechanism. Segmentation is the process of partitioning the image into sets of pixels/voxels that belong to the same class for the purpose of simplifying analysis. In medical images, these sets tend to represent differing tissue types. Segmentation can be applied in that context to exclude organs/tissues which are not being addressed in a particular analysis (for our example, only looking at the brain to identify Intracranial Hemorrhage and not skull, skin, muscle) using a myriad of techniques (e.g. thresholding, clustering, watershed, etc).

For example, in some embodiments, segmentation may be implemented using a thresholding operation. For each image, all pixels with a value greater than or less than a pair of Hounsfield Unit (HU) thresholds are removed (or rendered trivial by, e.g., replacing with zero). For ICH, it may be desirable to remove all pixels with a value of below 0 and above 100, since all relevant brain tissue and blood may be expected to be represented by pixels with HU values within this range.

In some embodiments, preprocessing may include normalization of scan data. One technique for data normalization is image resampling. For example, scan volumes may not all be acquired at the same resolution. Application of upsampling or downsampling may be used to normalize resolution. This can be done in a 2D or 3D space, using various interpolation methods (linear, splines, or other basis functions). In some embodiments, images can be resampled using the DICOM PixelSpacing field so that the area represented by the distance between a pair of pixels is the same. However, if the pixel spacings in the dataset are relatively uniform to begin with, such resampling may not be necessary or beneficial.

Data normalization mechanisms may also include cropping or padding operations. The extent of the scans (field of view) in physical/anatomical space may also differ, and will preferably be brought to uniformity. A determination can be made as to whether the edges or borders of the scan contain useful information, defining an optimal field of view or size of image. Then, the pixel (or, for volumetric images, voxels) at each border can be deleted if the scan is too large (or zero pixels/voxels can be added if the scan is too small) until the scans are of uniform size.

Other normalization mechanisms that may be utilized include featurewise or samplewise normalization. The value of each pixel can then be divided by the sum standard deviation of the pixel values and some epsilon (in order to avoid division by 0 if the standard deviation of the pixels in an image after thresholding is 0). In some embodiments, it may be desirable to use an epsilon of $1 \times 10^{-7}$. Employing featurewise normalization embodiments, for each pixel location in an image, one may subtract the mean and divide by the standard deviation, of the given pixel location across all images in the dataset. With samplewise normalization, the same calculation can be applied using the mean and standard deviation of all the pixels in that particular image, instead. These featurewise and samplewise normalization mechanisms can be used alone or together. In some embodiments, it may be desirable to apply one or more of these featurewise and/or samplewise normalization mechanisms as a final preprocessing step, after other preprocessing steps and immediately before training is commenced.

A blurring or smoothing operation can be performed to reduce noise and remove stray pixels not relevant to the anomaly detection task but not successfully removed by the thresholding operation It may also be desirable to optimize image alignment. In some embodiments, a rigid registration mechanism may be employed. Each patient is scanned in a slightly different orientation, which may affect the training of the models. A realignment of each scan to a given reference scan may increase the effectiveness of training/prediction. This can be done by optimizing on a given metric (least squares, mutual information, etc.) with respect to application of an affine transformation matrix, which "rotates" and "slides" the 3D volume into the optimal alignment.

In other embodiments, a deformable registration technique may be utilized to optimize image alignment. Each patient's anatomy is typically different from that of others, with respect to size, shape, and internal rotations. Deformable registration endeavors to re-map images to aligned key anatomic features, thereby increasing effectiveness of training/prediction. Deformable registration differs from rigid registration in that it applies "stretching/shrinking/bending" using demons or vector fields algorithms.

After a training dataset is extracted, conditioned and preprocessed, detection component training can take place. FIG. 8 illustrates an exemplary training process. Using the array of series level metadata generated as described above, in step S800, a subset of series Ds (typically, some percentage of the total available series Ds) is selected at random to include in the training set; the remaining series Ds can be used for a validation set. For ICH, it may be desirable to use a standard split of 80% of the total dataset for training and 20% for validation.

In step S810, training of a slice-level model (e.g. 2D CNN 310) is initiated. The slice-level model can be trained in step S810 by iterating over an array containing the Ds of series for which slice-level annotations exist. If a series ID was included in the series-level training set, the slices from that series can be added to a 3D (number of slices×height×width) array of training image data for the slice-level model, and their corresponding binary indicators of slice-level anomaly evidence can be added to a 10 (number of slices) array of training labels. If a given series ID was not in the series-level training set, the images can be added to an array of validation images for the slice-level model (with the corresponding labels added to an array of validation labels). In an exemplary ICH application, image arrays are N×64×64 and the label array is of length N, with each member of the validation array being either a 1 or 0 indicating whether the radiologist had marked that slice as containing a bleed.

In some embodiments, such as for models trained to detect anomaly location, training data may include an annotation of anomaly location in each slice. The annotation may be a 3D array (number of slices×height×width), with each voxel marked with a 0 or 1 depending on whether that voxel is contained in the anomaly.

In step S820, the slice-level model is specified. In some embodiments, this model is a convolutional neural network (CNN) with an input dimension of (1×height×width) and an output dimension of (1), corresponding to the estimated probability of the given image containing evidence of an anomaly. In other embodiments, the output may be a 2D array having a dimension of (height×width) with each unit in the output corresponding to the probability that a given pixel is contained in the anomaly. In yet other embodiments, as described above, a first output may be utilized for training the slice-level model, while a different output may be utilized to feed a subsequent model, such as a LSTM or other RNN.

Figure 9:
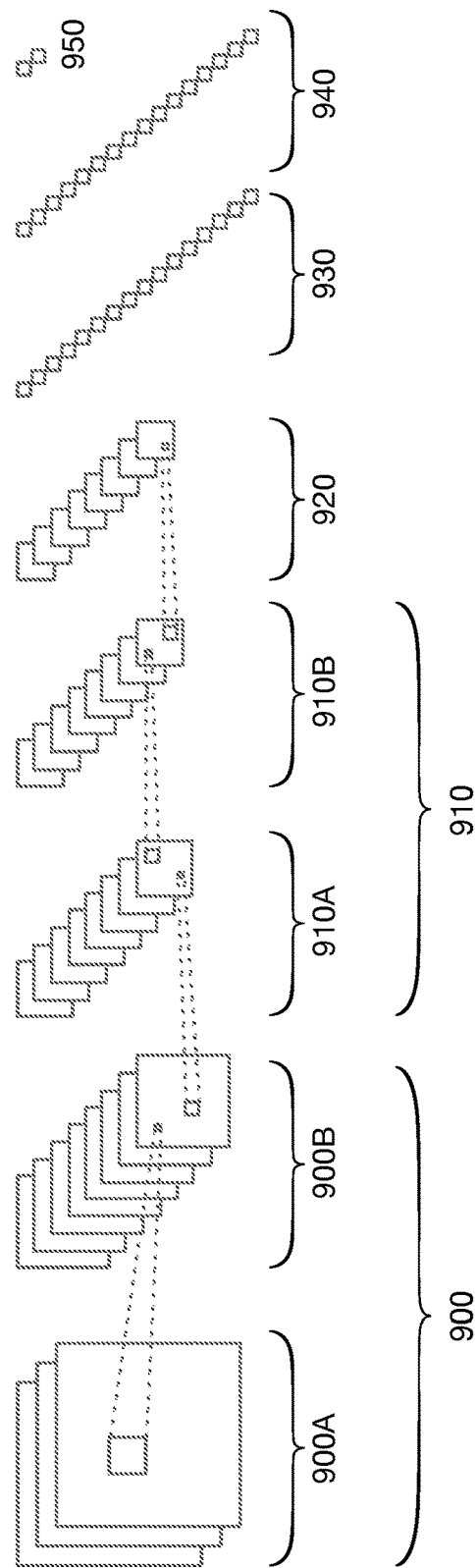
FIG. 9 is a schematic diagram of a convolutional neural network-based slice-level model.

For yet another exemplary model that may be useful in ICH applications, illustrated in FIG. 9, the CNN may have two stacked convolutional units 900 and 910. Convolutional unit 900 includes PReLU activated 5×5 convolution kernel 900A 3@32×32 input, followed by max pooling layer 900B receiving 32@18×18 feature maps. Convolutional unit 910 includes PReLU activated 5×5 convolution kernel 910A with 32@10×10 feature maps, followed by max pooling layer 910B receiving 48@6×6 feature maps. Flatten layer 920 includes 48@4×4 feature maps. These are followed by fully-connected hidden ReLU activated dense layers 930 (which may include 768 units) and dense layer 940 (which may include 512 units), a dense sigmoid activated output layer 950 with 1 or 2 neurons, depending on desired output content. The convolution layers have a border mode of "same", though "valid" could be used provided the appropriate zero-padding is applied between layers. The CNN can be trained to optimize a binary cross-entropy loss using the Adam optimizer with Nesterov momentum and a learning rate of 0.0001.

In step S830, the slice-level model is trained on the training images and labels, and validated on the validation images and labels for a set number of epochs. Every X epochs, augmentation can be applied to the training images. Examples of augmentation mechanisms include, without limitation, one or more of: rotating, translating, and/or flipping the images by a random amount, randomly zooming or cropping images, and/or applying a shear transformation. Every epoch, it may be desirable to check if the current validation loss is better than the previous validation loss. If so, the weights for each layer of the current version of the model can be saved before continuing. For an exemplary ICH application, it may be desirable to randomly rotate and translate the training images every 2 epochs and keep track of both cross-entropy loss and AUC, saving models if they produced the best result so far on either of those two metrics.

An alternative to training the slice-level model in the supervised manner described above would be to train it in an unsupervised manner, such as training an autoencoder to compress, degrade, and reconstruct the slices. This may produce worse results than the supervised training, but may be a sufficient alternative for training a slice-level model when slice-level annotations are not available.

In step S840, training of a series-level model is initiated. For example, in some embodiments, the system can iterate over the series Ds in the training set. For each series ID, all slices associated with the series can be retrieved as a 3D (number of slices×height×width) array. If the number of slices (slice_cnt) in the series is less than the maximum number of slices defined in the inclusion criteria (max_len), the array may be padded with a 3D ((max_len−slice_cnt)×height×width) arrays of zeros, such that the resulting array representing the series has dimensions of (max_len×height×width). This array may be appended to a 4D array of dimensions (number of series×max_len×height×width) containing the series to be used for training. The corresponding label for the series (i.e. binary indicator of whether it contains an anomaly) may be appended to an array of training labels. In some embodiments, the label array may be one-dimensional (i.e. dimensioned by the number of series); in other embodiments, such as when using a series-level model to predict the presence of an anomaly slice-by-slice, the array may be 2D (i.e. number of series×max_len). In any event, this entire process can be repeated, iterating over the validation set series IDs to construct arrays for validation series and labels.

In an exemplary ICH application, a max_len may be specified as 154, so the training and validation series arrays were (number of series×154×64×64). Labels may be, for example, a binary indicator of whether a series contained evidence of ICH or a multi-dimensional indication of anomaly location with each slice.

In step S850, the slice-level model is loaded. There are two primary ways of using this model: as a standalone feature extractor or integrated into the recurrent series-level model (described below) as a single model with both convolutional and recurrent layers.

To use the slice-level model as a feature extractor, a new model object can be instantiated that is architecturally identical to the slice-level model previously trained except that it doesn't have an output layer. This mode of operation is described generally above in connection with FIGS. 5 and 6, with further details of some embodiments as follows. More specifically, the weights can be loaded for all of the remaining layers from the "best loss" weights saved previously. Now, instead of outputting a single number corresponding to the probability that a given slice contains evidence of an anomaly, the model will output an array with length equal to the number of hidden nodes of the layer immediately preceding the output layer in the original slice-level model (encoding_dim). This array can be thought of as a set of automatically extracted features relevant to the anomaly determination. In the exemplary ICH application of FIG. 9, the layer 940 immediately preceding the output layer in our slice-level model was a dense layer with, e.g., 512 hidden nodes, so the encoding_dim was 512.

Figure 10:
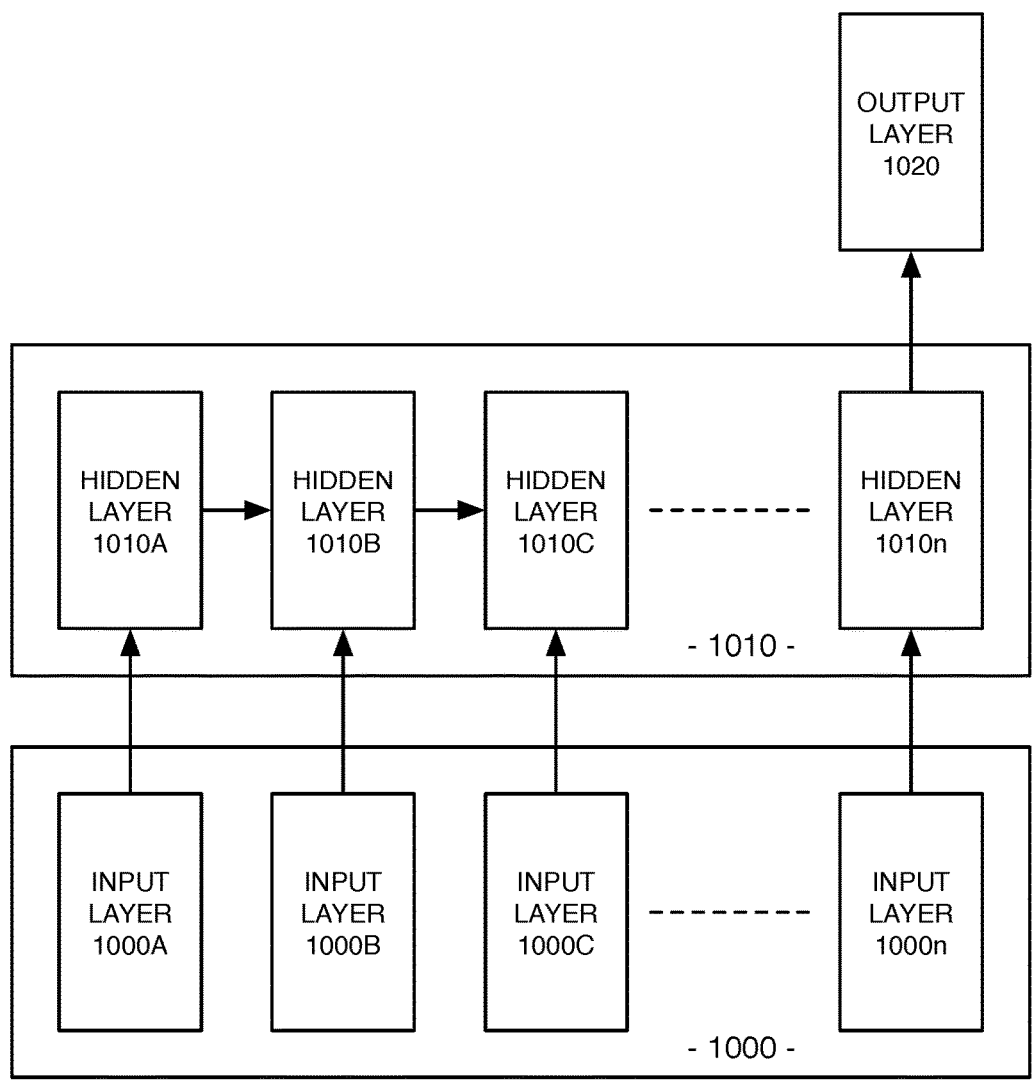
FIG. 10 is a schematic block diagram of a recurrent neural network-based series-level model with a per-series anomaly indicium.

In step S860, a series-level model is specified. In one exemplary embodiment, the series level model will be a recurrent neural network (RNN) with an input dimension of (max_len, encoding_dim) and an output shape of (1), corresponding to the estimated probability of the given series containing an anomaly. Of course, as with slice-level labels that may include a single, per-series anomaly indicia or per-slice indicia, other types of labels may be used at the series-level to yield other output shapes FIG. 10 illustrates a RNN having a per-series anomaly indicia. In an exemplary ICH application, the first layer of the RNN 1000 may be a masking layer, which instructs the network to ignore any input tensor whose values are all zero. Each first layer element 1000A to 1000n receives one slice from the CT series. For example, if the RNN is fed a series that has a slice_cnt of 96 but was padded with 2D zero matrices until it had a length of 154, the RNN with masking would ignore the last 58 slices. This method of padding all series to a uniform length and instructing the network to ignore the padded values allows the network to handle series of variable lengths. The next layer 1010 may be a long short-term memory (LSTM) layer, a variant of recurrent layers that excels at modeling long-term dependencies in a sequence. Optionally, more LSTM and dense layers can be added after, potentially including placement of a layer of dropout between them as a regularizer and/or having dropouts internally in each LSTM layer between the recurrent connections. The final layer 1020 outputs a series-level determination. In an exemplary embodiment, output layer 1020 may be a dense layer with sigmoid activation and one hidden unit, corresponding to the probability that a series contains ICH. The network can be trained to optimize a binary cross-entropy loss using the Adam optimizer with Nesterov momentum and a learning rate of 0.00005.

Figure 11:
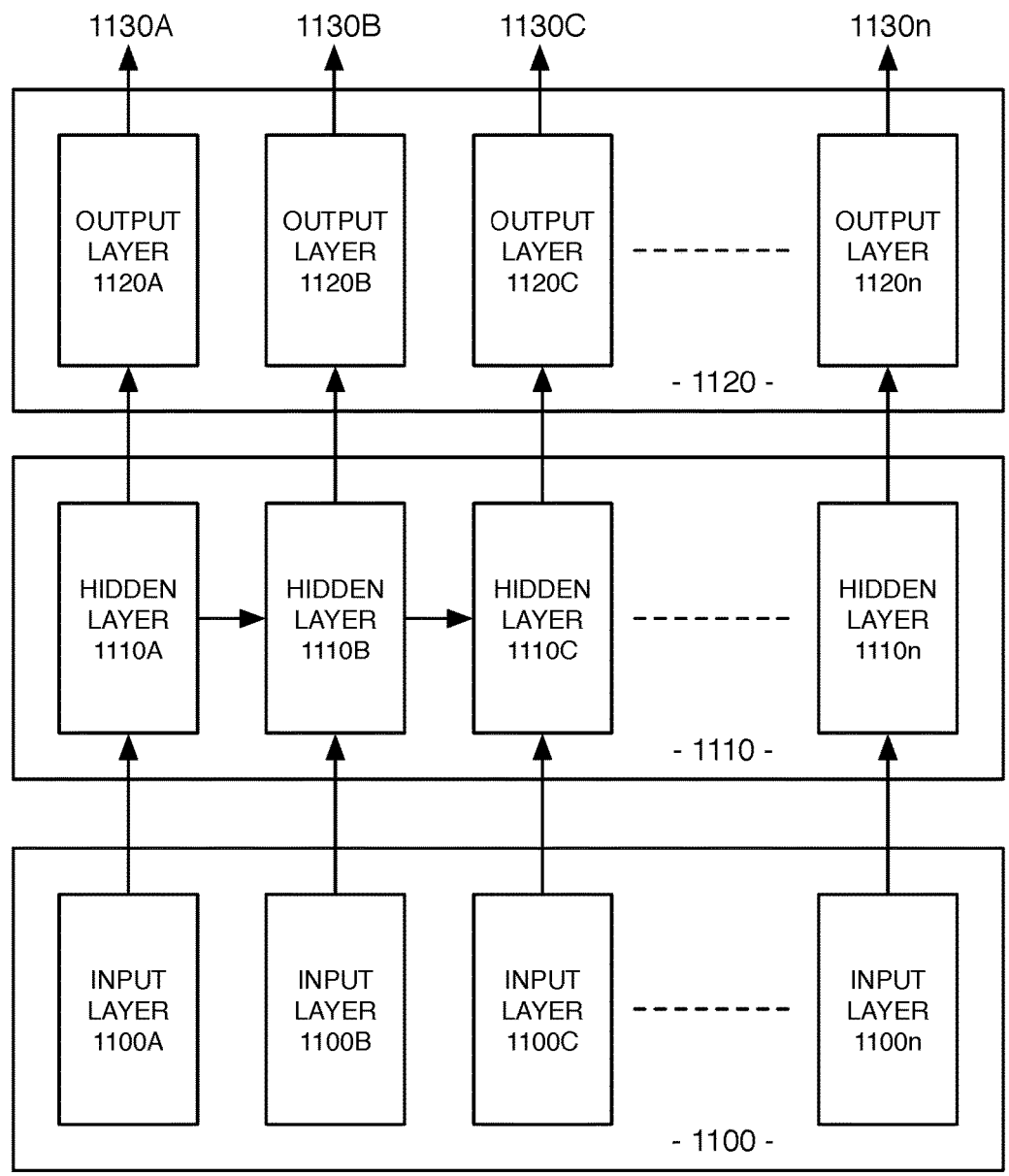
FIG. 11 is a schematic block diagram of a recurrent neural network-based series-level model with both per-slice and per-series anomaly indicia.

FIG. 11 illustrates an alternative embodiment of an RNN, configured to output determinations for each slice (e.g. likelihood that each individual slice indicates an intracranial hemorrhage). The RNN of FIG. 11 includes input layer 1100 (with elements 1100A to 1100n), a hidden layer 1110 (with elements 1100A to 1100n), and an output layer having multiple elements 1120A-1120n. Thus, outputs 1130 can collectively provide determinations concerning each input slice. Yet other RNN variations may utilize more modules, and output both determinations for each slice as well as determinations associated with the series as a whole (e.g. likelihood that the CT series as a whole exhibits an intracranial bleed).

In step S865, the feature extractor can be run on each non-padding slice in each series in the validation set, replacing every non-padding slice with the encoding_dim length output of the feature extractor and every padding slice with an encoding_dim length array of zeros.

In step S870, the series-level model is trained on the training series and labels and validated on the feature extracted validation series and labels for a set number of epochs. Every X epochs, augmentation can be applied to the training series. As applied above, exemplary augmentation mechanisms may include, without limitation, one or more of: rotating, translating, and/or flipping each slice in them by a random amount, randomly cropping and/or zooming slices, and applying a shear transformation. After augmentation, the feature extraction process is applied to the augmented training series before feeding them into the network. Every epoch, a determination is made whether the current validation loss is better than the previous validation loss. If so, the weights for each layer of the current version of the model are saved before continuing.

In applications detecting anomalies in volumetric images, such as medical CT or MRI scans, certain mechanisms for parameter optimization may be beneficial in configuring and training the CNN and RNN models. The values of hyperparameters may be beneficially optimized through manual or automated techniques; such parameters may include one or more of: number of layers, hidden node count per layer, augmentation frequency, types and severity of augmentation, learning rate, placement of dropout between layers, strength of dropout, batch size, convolutional kernel size, and optimizer or maximum sequence length. Parameters to which the ability of the model to converge is highly sensitive (such as learning rate or number and types of layers) may be best tuned manually. Others, such as amount of dropout and hidden node count, may be tuned with an automated procedure such as a random search over possible hyperparameter values with corresponding measurements of accuracy. For example, in an exemplary ICH application, the training images can be randomly rotated and translated every 2 epochs, and the analysis may keep track of cross-entropy loss, AUC, sensitivity at 90% specificity, and specificity at 90% sensitivity, saving models if they produced the best result so far on any of these metrics. Improvements in the series level model have been obtained by increasing the batch size from 1 to 8, dropping the learning rate from 0.001 to 0.00005, increasing the number of LSTM layers from 1 to 2, adding a layer of dropout with a dropout probability of 0.4 between these layers, using an Adam optimizer with Nesterov momentum (rather than traditional stochastic gradient descent), and increasing the number of hidden nodes in each LSTM layer from 256 to 1024.

Application: Detection of Intracranial Hemorrhage

A 2DCNN-LSTM model as described above was applied to a dataset of 3,341 CT scans of the brain, with 34.3% of the scans containing ICH. The scans had been completely de-identified and annotations were drawn around all instances of ICH by radiologists. The data was randomly split by patient into a training and validation set, with 2,656 scans used for training and 685 scans used for validation. The trained model achieved 91% sensitivity at 91% specificity, with area under the curve of 0.953 and a 0.233 log loss.

Application: False Positive Reduction in Chest CT Lung Nodule Detection

One application of mechanisms described herein for anomaly detection in volumetric images is reduction of false positives in lung nodule detection on chest CTs. Early detection of cancer on chest CTs can lead to improved outcomes for patients with lung cancer. To facilitate faster and more accurate interpretation, computer-aided detection systems may be utilized to detect lung nodules, which may represent early lung cancers. However, common commercial systems are typically hampered by low sensitivities and high false positive rates.

A classification ensemble as described herein was applied to the public Lung Imaging Database Consortium data set. This dataset, as adapted for the test case, consists of 888 lung CT scans with an average of 1.3 nodules per scan, taken with a wide range of acquisition protocols and annotated by a panel of four experienced radiologists. One aspect of the trial involved false positive reduction (FPR), in which a list of algorithmically-generated nodule candidate locations were provided, with the task of assigning each location a probability of being contained within a true nodule. The candidate list has a high sensitivity of 94.4%, but an average of 618.8 false positives (FPs) per scan. A high false positive rate has significant clinical ramifications, such as expenditure of significant radiologist time excluding areas detected by the software that are not actual nodules. Because of this, existing CAD systems have actually increased interpretation times, inhibiting their adoption.

The FPR challenge was framed as a binary classification problem. 3D patches were extracted around each candidate location. A model was trained to evaluate the probability of each candidate being contained within a nodule based on its corresponding patch. An ensemble of models was employed. The ensemble included several 3D CNNs (a standard approach to this type of problem), as well as several models using the deep learning architecture described above (having a combination of 2D CNNs and RNNs). The 2D CNN was trained to detect evidence of disease in the individual slices of a 3D image (e.g. a CT scan). The trained 2D CNN model was then used, with its output layer removed, as a feature extractor to encode each slice of a 3D image as a fixed-length feature vector. The encoded output was applied to a LSTM RNN, which was trained to detect evidence of disease in a volumetric image as a whole using the set of volumetric images represented as a sequence of encoded slices.

The ensemble consisted of six models: three 3D CNNs and three CNN-LSTMs. Each model used patches of different sizes around a given candidate location, giving each model a unique area of context around the candidate to work with. The 2D CNNs were adopted from ICH applications, described elsewhere herein, with 4 convolutional layers with max pooling and dropout in between, followed by two fully connected layers. The LSTM networks had 2 LSTM layers with intra-recurrent-layer dropout followed by one fully connected output layer. Little hyper-parameter tuning was performed apart from ensuring that the model converged; no grid or random hyper-parameter search procedures were used. In order to improve class balance in the dataset and reduce overfitting, the dataset was artificially augmented with synthetic positive patches created by translating and rotating the original positives from the dataset until the ratio of positives to negatives in the augmented dataset was 3:1. Every model in the ensemble was trained to minimize cross-entropy loss. Results were analyzed using Free Response Operating Characteristic analysis. To generate ensemble predictions, the geometric mean of the predictions of the individual models in the ensemble was taken.

In the end, the ensemble performed better than any individual model. Using predictions from both the 3D CNN architectures and the 2DCNN-LSTM architectures yielded better results than either architecture on their own. Metadata about, and results from, each model in the ensemble are illustrated in FIG. 12. It is believed that additional work (e.g. on hyper-parameter optimization, and/or use of a preprocessing step that resamples scans to reference an isotropic voxel dimension of about 1 mm) would yield even better results.

Application: Detection of Lung Nodules in Chest CT

In addition to using CNN-RNN models for false positive reduction, such models have also been incorporated with other models into an integrated lesion detection system. In one such application, a U-Net fully convolutional neural network architecture was utilized for candidate generation. For training and validation, the above-described lung CT dataset was randomly split by patient into a training set of 800 scans and a validation set of 88 scans. A preprocessing step was added, resampling the scans to a reference isotropic voxel dimension of 1 mm before training any models.

Using only slices containing nodules, 2D U-Net models were trained to predict each individual pixel's probability of being part of a nodule. Each input-pair shown to a model during training consisted of a 512×512 CT slice as the input and a 512×512 binary pixel mask with nodule pixels having a value of 1 and all others having a value of 0. Model output consisted of a 512×512 probability mask, with each value being the probability of the corresponding pixel in the input slice being part of a nodule. Dice's coefficient was used to evaluate the model's performance; the models were trained to minimize the negative of the Dice coefficient. Various model architectures were trained, having 5 or 6 contraction and expansion units, and filters per convolution layer ranging from 64 to 1024. Processing operations included batch normalization, as well as rotation and translation augmentations.

Three U-Net models for candidate generation were combined in a candidate generation ensemble with a classification threshold of 9.9e-5, yielding a sensitivity of 97.1% with 175.1 false positives per scan. The lung nodule FPR ensemble, described above, was then retrained using candidates generated by the final candidate generation ensemble, to yield even better performance for an end-to-end lesion detection system.

While the foregoing description describes methods and apparatuses that may be effectively utilized in a variety of applications, it is contemplated and understood that variations may be readily implemented by persons of skill in the art. In accordance with one such variation, as mentioned previously, an alternative to using the slice-level model as a standalone feature extractor is attaching it to the RNN directly, resulting in an "end-to-end" model with both convolutional and recurrent layers. This would involve specifying a model with the feature extractor network as previously described attached to and feeding into the RNN as previously described, and then loading the weights of the feature extractor portion of the network before training the CNN-RNN sequence as a whole. A primary benefit of doing this may be further tuning the convolutional layers beyond what they were able to learn by looking at individual slices in a vacuum, giving them a window into the context around slices. Moreover, specifying such a model and attempting to train it without loading weights from a previously trained convolutional network may result in a model completely unable to learn due to its depth. Disadvantages may include greater computational intensity than just using the slice-level model as a standalone feature extractor, and greater difficulty in manipulating or modifying the data while it's passing through the modeling pipeline. Integrating the slice-level and series-level models in the way described here may also present challenges in implementing the masking layer in between them, since the masking layer requires every value in the matrices being masked to be 0 and this is easier to control when the output of the convolutional layers is static, as it is when the CNN is used a standalone feature extractor.

In accordance with another contemplated variation, as alternative to the RNN outputting a single probability of an entire series containing an anomaly, the output layer may instead produce a sequence of numbers the same length as the number of slices, corresponding to the probability that each slice contains evidence of the anomaly. This may lead to a small but marked improvement in identifying evidence of anomalies on a slice-by-slice basis. In other variations, the output may also be "heat maps" of each slice indicating where the evidence of the anomaly might be, although such output may require post-processing to be diagnostically useful.

While certain embodiments of the invention have been described herein in detail for purposes of clarity and understanding, the foregoing description and Figures merely explain and illustrate the present invention and the present invention is not limited thereto.

The invention claimed is:

1. A computer-implemented method for detecting anomalies in volumetric medical images, the method comprising:
    training an initial computer-implemented two-dimensional regular convolutional neural network (CNN) using a training set comprising volumetric medical images, each comprising a spaced sequence of two-dimensional slice images taken along a defined axis, and a first set of slice-level labels comprising indications of anomalies; and
    training a recurrent neural network (RNN) using an RNN training set comprising encoded volumetric medical images and a corresponding second set of labels comprising indications of anomalies, each encoded volumetric medical image comprising a sequence of spaced two-dimensional slice images taken along a defined axis, in which:
        the encoded volumetric medical images each comprising a spaced sequence of two-dimensional slice images taken along a defined axis and encoded by a modified CNN; and
        the modified CNN comprises the trained initial CNN having an output layer removed, leaving a last dense layer prior to the removed output layer as a new output layer, such that each encoded slice has the dimension of the new output layer.

2. The method of claim 1, in which the first set of slice-level labels comprise a binary indicator of whether a slice contains evidence of a disease.

3. The method of claim 1, in which the first set of slice-level labels comprise a segmentation mask marking evidence of a disease in a slice.

4. The method of claim 1, in which the RNN is a Long Short-Term Memory RNN.

5. The method of claim 1, in which the second set of labels comprises a single series-level label.

6. The method of claim 5, in which the single series-level label comprises an indication of whether a volumetric image contains a given disease.

7. The method of claim 6, in which the RNN output comprises a probability that a given volumetric image contains the given disease.

8. The method of claim 1, in which the second set of labels comprises a sequence of slice-level indicators of the presence of a given disease.

9. The method of claim 8, in which the RNN output comprises slice-by-slice probabilities of the presence of the given disease.

10. The method of claim 8, in which the RNN output comprises a segmentation map indicative of disease location.

11. A computer-implemented method for detecting anomalies in volumetric medical images, the method comprising: determining initial coefficients for a regular convolutional neural network (CNN) that is part of a neural network sequence comprised of the regular CNN and a recurrent neural network (RNN) where the regular CNN has an output layer feeding an input layer of the RNN, the initial coefficients determined at least in part by training an initial CNN as a feature extractor using 2D medical images; loading initial coefficients into the regular CNN portion of the neural network sequence; and training the neural network sequence as a whole using a training set of volumetric medical images each comprising a spaced sequence of two-dimensional slice images taken along a defined axis, and a corresponding set of training labels indicative of anomalies within the volumetric images.

12. The method of claim 11, in which the regular CNN comprises an output layer that is a final dense layer.

13. The method of claim 11, in which the training labels comprise, for each volumetric image, a binary indicator of whether the volumetric image contains evidence of a disease.

14. The method of claim 11, in which the training labels comprise, for each volumetric image, a segmentation mask marking evidence of a disease in the volumetric image.

15. The method of claim 11, in which the RNN is a Long Short-Term Memory RNN.

16. The method of claim 11, further comprising:
    applying a volumetric medical image to the neural network sequence input, and generating a resulting output associated with the detection of an anomaly in the volumetric medical image.

17. The method of claim 16, in which the neural network sequence output comprises a probability that a given volumetric image contains evidence of a given disease.

18. The method of claim 16, in which the neural network sequence output comprises a segmentation map indicative of disease location.

* * * * *